US008835438B2

(12) United States Patent
Ishiyama

(10) Patent No.: US 8,835,438 B2
(45) Date of Patent: Sep. 16, 2014

(54) METHOD OF TREATING MEMORY/LEARNING DYSFUNCTIONS CAUSED BY SCHIZOPHRENIA WITH LURASIDONE

(75) Inventor: Takeo Ishiyama, Suita (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 8 days.

(21) Appl. No.: 12/401,958

(22) Filed: Mar. 11, 2009

(65) Prior Publication Data

US 2009/0176800 A1 Jul. 9, 2009

Related U.S. Application Data

(62) Division of application No. 10/589,804, filed as application No. PCT/JP2005/002838 on Feb. 16, 2005, now abandoned.

(30) Foreign Application Priority Data

Feb. 20, 2004 (JP) ................. 2004-044986

(51) Int. Cl.
A61K 31/497 (2006.01)
A61K 31/554 (2006.01)
A61K 31/496 (2006.01)
A61K 31/5513 (2006.01)
A61K 31/445 (2006.01)
G01N 33/50 (2006.01)
C07D 417/12 (2006.01)

(52) U.S. Cl.
CPC .......... G01N 33/5088 (2013.01); A61K 31/554 (2013.01); A61K 31/496 (2013.01); A61K 31/5513 (2013.01); A61K 31/445 (2013.01); C07D 417/12 (2013.01)
USPC .................................................. 514/254.04

(58) Field of Classification Search
USPC .................................................. 514/254.04
See application file for complete search history.

(56) References Cited

U.S. PATENT DOCUMENTS

| 5,444,073 | A | 8/1995 | Perregaard et al. |
| 5,532,372 | A | 7/1996 | Saji et al. |
| 5,780,632 | A | 7/1998 | Saji et al. |
| 6,964,962 | B2 | 11/2005 | Wong et al. |
| 7,067,507 | B2 | 6/2006 | Pulley et al. |
| 2003/0050307 | A1 | 3/2003 | Ruhland et al. |
| 2006/0025422 | A1 | 2/2006 | Nakamura et al. |
| 2006/0111429 | A1 | 5/2006 | Fish et al. |
| 2006/0142276 | A1 | 6/2006 | Ohno et al. |
| 2008/0255148 | A1 | 10/2008 | Ohno et al. |
| 2009/0176800 | A1 | 7/2009 | Ishiyama |
| 2010/0105692 | A1 | 4/2010 | Moheno et al. |

FOREIGN PATENT DOCUMENTS

| EP | 0 464 846 A1 | 1/1992 |
| JP | 05-17440 A | 1/1993 |
| JP | 6-504787 A | 6/1994 |
| JP | 08-333368 | 12/1996 |
| JP | 2000-281576 | 10/2000 |
| JP | 2003-135074 A | 5/2003 |
| JP | 2003-160583 | 6/2003 |
| JP | 2003-519226 A | 6/2003 |
| WO | WO 93/16073 | 8/1993 |
| WO | WO 95/34306 | 12/1995 |
| WO | WO 96/14297 | 5/1996 |
| WO | WO 99/52519 | 10/1999 |
| WO | WO 02/22581 A1 | 3/2002 |
| WO | WO 02/24166 A1 | 3/2002 |
| WO | WO 03/066039 A1 | 8/2003 |
| WO | WO 2004/017973 | 3/2004 |
| WO | WO 2004/113333 | 12/2004 |
| WO | WO 2007/124757 A2 | 11/2007 |
| WO | WO 2008/124030 | 10/2008 |

OTHER PUBLICATIONS

Malenka et al., Science, vol. 285, pp. 1870-1874, (Sep. 17, 1999).
Myhrer, Brain Research Reviews, vol. 41, pp. 268-287, (2003).
Krystal et al., Psychopharmacology, vol. 169, pp. 215-233, (2003).
Goff et al., Am. J. Psychiatry, vol. 158, No. 9, pp. 1367-1377, (Sep. 2001).
Ibrahim et al., Am. J. Psychiatry, vol. 159, No. 11, pp. 1811-1823, (Nov. 2000).
Clinton et al., Am. J. Psychiatry, vol. 160, No. 6, pp. 1100-1109, (Jun. 2003).
Clinton et al., Society for Neuroscience Program No. 754.4, (2003). (online) (abstract only).
Cloninger, Proc. Natl. Acad. Sci., vol. 99, No. 21, pp. 13365-13367, (Oct. 15, 2002).
Moghaddam, Neuron, vol. 40, pp. 881-884, (Dec. 4, 2003).
Harvey et al., Psychopharmacology, vol. 169, pp. 213-214, (2003).
Meltzer et al., Proc. Natl. Acad. Sci., vol. 96, No. 24, pp. 13591-13593, (Nov. 23, 1999).
Kasper et al. Psychoneuroendocrinology, vol. 28, pp. 27-38, (2003).
Sharma et al., Psychiatr. Clin. N. Am., vol. 26, pp. 25-40, (2003).
Weiss et al., Psyhopharmacology, vol. 162, pp. 11-17, (2002).
Hyman et al., Science, vol. 299, pp. 350-351, (Jan. 17, 2003).
Geyer et al., Progress in Neuro-Psychopharmacology & Biological Psychiatry, vol. 27, pp. 1071-1079, (2003).
Nakagawa et al., Brain Research vol. 706, pp. 227-232, (1996).

(Continued)

Primary Examiner — Paul Zarek
(74) Attorney, Agent, or Firm — Finnegan, Henderson, Farabow, Garrett & Dunner, LLP

(57) ABSTRACT

A method of evaluating memory/learning functions with the use of a model with glutamic acid N-methyl-D-aspartate (NMDA) type receptor hypofunction as an animal model for schizophrenia and with the use of reference memory task, wherein there has been found concrete means for detecting any differences in activity between typical anti-psychosis drugs and atypical anti-psychosis drugs is found.

An in vivo animal model for screening of a therapeutic agent for improving cognitive dysfunction by schizophrenia is provided.

3 Claims, No Drawings

(56) References Cited

OTHER PUBLICATIONS

Harrod et al., Pharmacology, Biochemistry, and Behavior, vol. 69, pp. 585-593, (2001).
Mohn et al., Cell, vol. 98, pp. 427-436, (1999).
Miyamoto et al., Journal of Neuroscience, vol. 21, No. 2, pp. 750-757, (Jan. 15, 2001).
Harvey et al., J. Clin. Psychiatry, vol. 65, pp. 361-372, (2004).
Enomoto et al., Brain Science, vol. 25, No. 5, pp. 437-444 (2003).
Ebihara, Mitsuru et al., Togo Shicchosho no Dobutsu Model, Igaku no Ayumi, vol. 208, No. 3, pp. 138-142 (2004).
Shinkei Kairomo Keisei to Kofunsei Synapse Kasosei ni Kansura Kodogakuteki Kenkyu, pp. 13-20 (2003) with partial English language translation.
Noda, et al, Abstracts Society Neuroscience (2000) v. 26(1-2), p. 6533.
Didriksen, et al, Society Neuroscience Abstract (2002) v. 2002, abstract No. 893.1.
Corbett, Pharmacol Biochem Behav, (1995) v. 51(2-3), p. 561-564.
Wise, et al, Society Neuroscience Abstract (2002), v. 2002, abstract No. 494.7.
Puttrese, et al, Society Neuroscience Abstract (2003), v. 2003, abstract No. 964.19.
Tokuda, et al, J Pharmacol Sciences, (2004), v. 94, supplement 1, p. 163P.
Mettey Y, et al., "Synthesis of 11-Aminodibenzol[b,f][1,4]thiazepines and Fluoro Derivatives," Journal of Heterocyclic Chemistry, 03-04 (1997), 34, pp. 465-467.
Turetsky et al., "Memory-Delineated Subtypes of Schizophrenia: Relationship to Clinical, Neuroanatomical, and Neurophysiological Measures," *Neuropsychology* vol. 16, No. 4, pp. 481-490 (2002).
U.S. Appl. No. 10/525,021, filed Feb. 18, 2005.
Office Action in U.S. Appl. No. 10/525,021 mailed Dec. 17, 2007.
Office Action in U.S. Appl. No. 10/525,021 mailed Sep. 17, 2008.
Office Action in U.S. Appl. No. 10/525,021 mailed Jun. 12, 2009.
Office Action in U.S. Appl. No. 10/525,021 mailed Mar. 5, 2010.
U.S. Appl. No. 10/562,039, filed Dec. 22, 2005.
Office Action in U.S. Appl. No. 10/562,039 mailed Mar. 18, 2008.
Office Action in U.S. Appl. No. 12/140,927 (continuation of U.S. Appl. No. 10/562,039) mailed Oct. 3, 2008.
Office Action in U.S. Appl. No. 12/140,927 mailed Oct. 19, 2009.
Alphs, Larry, "An industry perspective on the NIMH Consensus Statement on negative symptoms," Schizophrenia Bulletin, vol. 32, No. 2, pp. 225-230, (2006).
Biederman, Joseph, et al., "Risperidone treatments for ADHD in children and adolescents with bipolar disorder," Neuropsychiatric Diseases and Treatment, vol. 4, No. 1, pp. 203-207 (2008).
Bruno, et al., The α2c-adrenergic receptor mediates hyperactivity of colobomo mice, a model of attention deficit hyperactivity disorder, Neurobiology of Disease, vol. 23, pp. 679-688, (2006).
Center for Drug Evaluation and Research, Pharmacology Reviews at FDA, pp. 1-260, (Oct. 2010).
English translation of Office Action from the Chinese Patent Office in Appln. No. 200480017534.X dated Jan. 29, 2010.
EP Search Report for European Patent Application No. 11160001.1-2123 dated Jul. 19, 2011.
Erhart, Stephen M., et al., "Treatment of schizophrenia negative symptoms: future prospects," Schizophrenia Bulletin, vol. 32, No. 2, pp. 234-237, 2006.
European Neuropsychopharmacology, "P.3.155 Efficacy of lurasidone (SM-13496) in the treatment of schizophrenia: results of two, phase 2, pacebo-controlled studies," vol. 15, pp. S522-S523, (2005).
International Search Report for International Application No. PCT/JP2011/062314 dated Jun. 28, 2011.
Ishiyama, T., et al., "Effects on sm-13496, a novel serotonin-dopamine antagonist, and other antipsychotics on cognitive performance in rat passive avoidance test," abstract, vol. 23, (2003).
Kane, John, "Commentary: Consensus statement on negative symptoms," Schizophrenia Bulletin, vol. 32, No. 2, pp. 223-224, (2006).

Kirkpatrick, Brian, et al., "The NIMH-MATRICS consensus statement on negative symptoms," vol. 32, No. 2, pp. 214-219, (2006).
Laughren, Thomas, et al., "Food and Drug Administration perspective on negative symptoms in schizophrenia as a target for a drug treatment claim," Schizophrenia Bulletin, vol. 32, No. 2, pp. 220-222, (2006).
Masi, Gabriele, et al., "Aripiprazole monotherapy in children and young adolescents with perfasive development disorders," CNS Drugs, vol. 23, No. 6, pp. 511-521, (2009).
Meyer, Jonathan, M. et al., "Lurasidone: a new drug in development for schizophrenia," Expert Opinion on Investigational Drugs, vol. 18, No. 11, pp. 1715-1726, (2006).
Notice of Allowance and Fees Due in U.S. Appl. No. 12/140,927, dated Dec. 1, 2011.
Office Action in U.S. Appl. No. 10/525,021 mailed Aug. 29, 2007.
Office Action in U.S. Appl. No. 10/589,804 mailed Dec. 11, 2008.
Office Action in U.S. Appl. No. 13/113,703, mailed Nov. 22, 2011.
Ogasa et al., "SM-13496 in patients with acute exacerbation of schizophrenia: A two-dose double-blind phase II comparison with placebo", Schizophrenia Research, vol. 60, No. 1, pp. 297, (2003).
Poster exhibited at the 18th European College of Neuropsychopharmacology Congress, Oct. 23-26, 2005.
Powell, Susan, B., et al., "RO-10-5824 is a selective dopamine D4 receptor agonist that increases novel object exploration in C57 mice," Neuropharmacology, vol. 44, pp. 473-481, (2003).
Protais, P. et al., "Climbing behavior induced by apomorphine in mice: a simple test for the study of dopamine receptors in striatum," Psychopharmacology, vol. 50, pp. 1-6, (1976).
Russell, Vivienne, A., et al., "Animal models of attention-deficit hyperactivity disorder," Behavioral and Brain Functions, vol. 1, No. 9, pp. 1-17, (2005).
Rutten, K., et al., "Selective PDE inhibitors rolipram and sildenafil improve object retrieval performance in adult cynomolgus macaques," Psychopharmacology, vol. 196, pp. 643-648, (2008).
Snyder, Peter J. et al., "Reversal of scopolamine-induced deficits with a single dose of donepezil, an acetylcholinesterase inhibitor," Alzheimer's & Dementia, vol. 1, pp. 126-135, (2005).
Wang, D., et al. "Synergistic effect of galantamine with risperidone on impairment of social interaction in phencyclidine-treated mice as a schophrenic animal model," Neuropharmacology, vol. 52, pp. 1179-1187 (2007).
Wise, L.E., et al., "Reversal learning in the 8—arm radial maze in rats is impaired by subchronic adminstration of the non-competitive NMDA antagonist ketamine", Society for Neuroscience, abstract, vol. 2002, (2002).
Woolley et al., "Selective dopamine D4 receptor agonist (A-412997) improves cognitive performance and stimulates motor activity without influencing reward-related behaviour in rat," Behavioural Pharmacology, vol. 19, Iss. 8, pp. 765-776, (Dec. 2008).
Approval Labeling Text, NDA 21-487, for NAMENDA™ (memantine hydrochloride) (2003).
Barber, Teresa A., et al., Memantine ameliorates scopolamine-induced amnesia in chicks trained on taste-avoidance learning, *Neurobiology of Learning and Memory*, vol. 93, pp. 540-545 (2010).
Bejar, Corina, et al., "Effect of rivastigmine on scopolamine-induced memory impairment in rats," *European Journal of Pharmacology*, vol. 383, pp. 231-240 (1999).
Botero, Hector M. et al., "Structure—Activity Relationships in a Series of Bisquaternary Bisphthalimidine Derivatives Modulating the Muscarinic $M_2$-Receptor Allosterically," J. Med. Chem. 43:2155-2164 (2000).
Bowen, D.M., "Traditional Pharmacotherapy May Succeed in Alzheimer's Disease," Trends in Neurosciences, 1992, vol. 15, No. 3, pp. 84-85.
"Delirium, Dementia, Amensia, Cognitive Disorders," http://www.nlm.nih.gov/cgi/mesh/2009/MB_cgi?mode=&term...
m,+Dementia,+Amnestic,+Cognitive+Disorders&field=entry, accessed Jul. 1, 2009.
Diagnostic and Statistical Manual of Mental Disorders, Fourth Edition (DSM-IV™) pp. 273-278, 285, and 286 (1994), published by the American Psychiatric Association, Washington D.C.

(56) References Cited

OTHER PUBLICATIONS

Doggrell, Sheila A. et al., "Treatment of Dementia With Neurotransmission Modulation," Expert Opinion on Investigational Drugs, 2003, 12(10), 1633-54.
Duka, Theodora, "Scopolamine-induced Amnesia in Humans: Lack of Effects of the Benzodiazepine Receptor Antagonist β-carboline ZK 93426," Journal of Psychopharmacology, 1992, vol. 6, No. 3, pp. 382-388, Abstract.
Emre, Murat, M.D. et al., "Rivastigmine for Dementia Associated with Parkinson's Disease," The New England Journal of Medicine, 2004, 351-24, pp. 2509-2518.
English translation of Second Office Action from the Chinese Patent Office in Appln. No. 20040017534.X dated Jan. 29, 2010.
English translation of Office Action from the Japanese Patent Office in Appln. No. 2005-507314 dated Jun. 29, 2010.
EP Official Action for Corresponding EP Application No. 04 746 564.6-2117 dated Nov. 20, 2009.
EP Official Action for Corresponding EP Application No. 04 746 564.6-2117 dated Aug. 27, 2010.
EP Search Report for European Patent Application No. 04746564.6 dated Mar. 2, 2009.
Fabre, Serge et al., "Protein Kinase C Inhibitors; Structure—Activity Relationships in K252c-Related Compounds," Bioorg. Med. Chem. 1(3):193-196 (1993).
Fernandez, Hubert H. et al., "Pharmacotherapy of dementia with Lewy bodies," Expert Opinion on Pharmacotherapy, 2003, 4(11), pp. 2027-2037.
Final Office Action in U.S. Appl. No. 12/140,927 dated Jul. 10, 2009.
Final Office Action in U.S. Appl. No. 12/140,927 dated Jul. 18, 2011.
Friedman, Joseph I., "Cholinergic targets for cognitive enhancement in schizophrenia: focus on cholinesterase inhibitors and muscarinic agonists," Psychopharmacology, 2004, 174, pp. 45-53.
International Search Report for International Application No. PCT/JP2004/009095 dated Aug. 24, 2004.
Ishizumi, Kikuo, et al., "Succinimide Derivatives. II. Synthesis and Antipsychotic Activity of N-[4-[4-(1,2-Benzisothiazol-3-yl)-1-piperazinyl]butyl]-1,2-cis-cyclohexanedicarboximade (SM-9018) and Related Compounds," Chem. Pharm. Bull. 43(12):2139-2151 (1995).
Japanese Office Action in corresponding Japanese Application No. 2006-510283 dated May 31, 2011.
Jellinger, Kurt A., "The Pathology of Ischemic-Vascular Dementia: an Update," Journal of the Neurological Sciences 203-204 (2002) pp. 153-157.
Kahle, Philipp J. et al., "The Emerging Utility of Animal Models of Chronic Neurodegenerative Diseases," Emerging Therapeutic Targets, 2001, 5(1), 125-132.
Kay, Stanley R. et al., The Positive and Negative Syndrome Scale (PANSS) for Schizophrenia, *Schizophrenia Bulletin*, vol. 13, No. 2, 1987, pp. 261-276.
The Lancet, "The Treatment of Senile Insanity," Lancet Limited, London, GB LNKD-D01:10.1016/S0140-6736 (01) 05083-8, vol. 208, No. 5381, Oct. 16, 1926, pp. 820-821.
Lindenmayer et al., *Psychiatric Quarterly*, vol. 65, No. 4, pp. 299-322 (1994).
Misane et al., "Selective 5-HT$_{1A}$ Antagonists WAY 10065 and NAD-299 Attenuate the Impairment of Passive Avoidance Caused by Scopolamine in the Rat, " *Neuropsychopharmacology* 28, pp. 253-264 (2003).
Miyachi, Hiroyuki et al., "Novel Biological Response Modifiers: Phthalimides with Tumor Necrosis Factor-α Production-Regulating Activity," J. Med. Chem. 40:2858-2865 (1997).
Nippon-Shinkei-Seishin-Yakurigaku Zasshi (JPn. J. Neuropsychopharmacol.) 23: 296 (2003).
Non-Final Office Action in U.S. Appl. No. 12/140,927 dated Nov. 10, 2010.
Norman, Mark H. et al., "Effect of Linking Bridge Modifications on the Antipsychotic Profile of Some Phthalimide and Isoindolinone Derivatives," Journal of Medical Chemistry, 1996, 39(1), 149-57.
Office Action in Japanese Application No. 2005-507314 issued on Jun. 29, 2010 (4 pages).
Parnetti, et al., "Cholinergic Precursors in the Treatment of Conitive Impairment of Vascular Origin: Ineffective approaches or need for re-evaluation?," Journal of the Neurological Sciences 257 (2007) 264-269.
*Perricone v. Medicis Pharm. Corp.*, 432 F.3d 1368 (Fed. Cir. 2005).
Perry, Elaine et al., "Acetylcholine in Mind: a Neurotransmitter Correlate of Consciousness?," TINS, vol. 22, No. 6, p. 273-280 (1999).
Prescribing Information for ARICEPT® (donepezil hydrochloride) (14 pages) (2010).
Prescribing information for "Exelon® (rivastigmine tartrate) Capsules and Oral Solution" (31 pages) (2006).
Reingold, Jennifer L. et al., "Rivastigmine for the Treatment of Dementia Associated with Parkinson's Disease," Neuropsychiatric Disease and Treatment 3:775-783 (2007).
Roman, Gustavo C. et al., "Donepezil in Vascular Dementia: Combined Analysis of Two Large-Scale Clinical Trials," Dementia and Geriat.. Cogn. Disord. 20:337-344 (2005).
Romero, Arthur G. et al., "Synthesis of Metabolically Stable Arylpiperazine 5-HT1A Receptor Agonists," Bioorganic & Medicinal Chemistry Letters, vol. 2, No. 12, pp. 1703-1706 (1992).
Small, David H., "Acetylcholinesterase Inhibitors for the Treatment of Dementia in Alzheimer's Disease: Do We Need New Inhibitors?," Expert Opinion on Emerging Drugs, 2005, 10(4), 817-823.
Takahashi, Satoshi et al., "Anti-Dementia Drugs and Vascular Dementia," Rinsho-Seishinigaku, (Clinical Psychiatry), 31 (10): 1189-1193 (2002).
Thomas, Elizabeth et al., "Specific Impairments in Visuospatial Working and Short-Term Memory Following Low-Dose Scopolamine Challenge in Healthy Older Adults," Neuropsychologia, vol. 46 (2008), pp. 2476-2484.
Tokita, Kenichi et al., "Combination of a Novel Antidementia Drug FK960 with Donepezil Synergistically Improves Memory Deficits in Rats," Pharmacology, Biochemistry and Behavior, vol. 73 (2002) pp. 511-519.
Xu Taixiang et al, "Status quo and Development of Alzheimer's Disease," *Acta Academiae Medicinae Qingdao Universitatis*, vol. 37, No. 4, p. 355-357 (2001).

METHOD OF TREATING MEMORY/LEARNING DYSFUNCTIONS CAUSED BY SCHIZOPHRENIA WITH LURASIDONE

RELATED APPLICATIONS

The present application is a Divisional application of U.S. application Ser. No. 10/589,804, filed Aug. 17, 2006 and now abandoned, which in turn is a National Stage application of International application PCT/JP2005/002832, filed Feb. 16, 2005. The International application PCT/JP2005/002832 in turn claims priority of Japanese application 2004-044986, filed Feb. 20, 2004. All of the above applications are hereby incorporated in their entirety by reference.

TECHNICAL FIELD

The present invention relates to an in vivo screening method of a therapeutic agent for improving memory/learning dysfunctions by schizophrenia.

BACKGROUND ART

Glutamic acid is a most popular excitatory neurotransmitter in the central nervous system, and the receptors thereof are classified broadly into an NMDA type, an α-amino-3-hydroxy-5-methyl-4-isoxazolepropionic (AMPA) type, a kainate type, and a metabotropic type. It is revealed that the NMDA type receptor plays an important role in the completion of the long-term potentiation (LTP), which is an electrophysiologically basal process of the memory/learning functions (cf., Science 285: 1870-1874 (1999)). At the animal level, it is known that an NMDA receptor antagonist may induce memory/learning dysfunctions in various memory/learning tasks such as a passive avoidance response, a radial maze, a T or Y maze, a water maze, a place or object recognition, an autoshaping learning task, and a lever-pressing task (cf., Brain Res Rev 41: 268-287 (2003)). It is also reported that PCP or ketamine, which is also an NMDA receptor antagonist, induces cognitive dysfunctions in humans (cf., Psychopharmacology 169: 215-233 (2003)). Namely, it is a common opinion among the electrophysiological level, the animal level and the human level that the NMDA type receptor plays an important rule in the memory/learning process.

It is the most widely-accepted hypothesis that the hypofunction of the NMDA type receptor is regarded as a mechanism of development of schizophrenia. This hypothesis is established based on the following four points:
(i) PCP and ketamine, which are an NMDA receptor antagonist, induce the major symptoms of schizophrenia in normal humans including cognitive dysfunction, positive negative symptoms, and induce the exacerbation of symptoms in patients with schizophrenia (cf., Am J Psychiatry 158: 1367-1377 (2001), Psychopharmacology 169: 215-233 (2003)):
(ii) There are clinical reports that glycine, D-serine and D-cycloserine, which have been known to elevate NMDA receptor functions, enhance the drug efficacy of anti-psychotic drugs in patients with schizophrenia, and improve negative symptoms and cognitive dysfunctions (cf., Am J Psychiatry 158: 1367-1377 (2001), Psycho-pharmacology 169: 215-233 (2003)):
(iii) The variation in the amount of glutamic acid per se, or the amount of the endogenous substance: N-acetyl-aspartyl glutamate (NAAG) having an NMDA antagonistic activity is observed in patients with schizophrenia (cf., Am J Psychiatry 158: 1367-1377 (2001)), and the change in the amount of mRNA and proteins of NMDA type receptor subunit and NMDA receptor-related protein is observed in patients with schizophrenia (cf., Am J Psychiatry 157: 1811-1823 (2000), Am J Psychiatry 160: 1100-1109 (2003), Society for Neuroscience Program No. 754.4. (2003)):
(iv) A series of genes which were found as a gene relating to the onset of schizophrenia (Neuregulin 1, G72, dysbindin, calcineurin) are genes being capable of modifying NMDA receptor functions (cf., Proc Natl Acad Sci USA 99: 13365-13367 (2002), Neuron 40: 881-884 (2003)). From the above facts, it is generally considered that the dysfunctions induced by NMDA type receptor antagonists are models to reflect the dysfunctions by schizophrenia.

Schizophrenia is associated with various cognitive dysfunctions such as attention, memory, learning, executive functions, but it is reported that among these functions, especially a certain memory function is selectively and seriously damaged. Namely, memory is classified broadly into procedural memory and declarative memory. The declarative memory is further classified into short-term memory/working memory and a long-term memory/reference memory. It is reported that in schizophrenia, the declarative memory including both of the working memory and the reference memory is selectively damaged, and further, among them, the damage of the reference memory is most serious. Recently, it is reported that the cognitive dysfunction including such a reference memory dysfunction is the most important predictive factor of social daily ability and professional ability, and a quality of life of patients with schizophrenia. Then, at the moment, the cognitive dysfunction is positioned as a core symptom of schizophrenia (cf., Psychopharmacology 169: 213-214 (2003), Proc Natl Acad Sci USA 96: 13591-13593 (2002), Psychoneuroendocrinology 28: 27-38 (2003), Psychiat Clin N Am 26: 25-40 (2003)). Under these circumstances, many clinical trials are being done with respect to the effects of the existing anti-psychotic agents on various cognitive dysfunctions by schizophrenia (cf., Psychopharmacology 162: 11-17 (2002), Psychoneuroendocrinology 28: 27-38 (2003), Psychiat Clin N Am 26: 25-40 (2003)), and there is being submitted an evidence that a typical anti-psychotic agent, haloperidol, is ineffective, while some of atypical anti-psychotic agents are effective (cf., J. Clin Psychiatry 65: 361-372, Psychoneuroendocrinology 28: 27-38 (2003), Psychiat Clin N Am 26: 25-40 (2003)). However, the drug efficacy of these existing drugs are not sufficient enough, and hence, it has been discussed that it is important to develop a therapeutic agent for cognitive dysfunctions by schizophrenia (cf., Science 299: 350-351 (2003)).

On the other hand, in the research and development of therapeutic agents for human diseases, it is generally essential to develop an animal model being suitable for screening thereof. In such an animal model, the face validity (similarities of symptoms), the construct validity (similarities of the mechanism of development of symptoms), and the predictive validity (predictability of clinical drug efficacy), and further, the easiness being suitable for screening are required. However, it is considered that an animal model for cognitive dysfunctions by schizophrenia satisfying such requirements is quite limited at the moment. Namely, as an animal model for schizophrenia being capable of satisfying the above-mentioned requirements, PCP-induced models showing prepulse inhibition or social interaction failure can be exemplified (cf., Prog Neuropsychopharmacol Biol Psychiaty 27: 1071-1079 (2003)). It is known that the drug efficacy of atypical anti-psychotic agents, but that of a typical anti-psychotic agent can be selectively detected in these models, and the results obtained in these animal models partially reflect the clinical effects of a drug on schizophrenia. However, it is considered that among these animal models the former one may reflect the disorder of the sensorimotor gating function in schizophrenia, while the latter may reflect the negative symptoms of schizophrenia such a social withdrawal. Thus, as mentioned above, an easy model for evaluating drug efficacy, (1) being capable of reflecting reference memory dysfunction, which is the most serious cognitive dysfunction in schizophrenia (i.e., face validity, similarities of symptoms); (2) being associated with NMDA receptor hypofunction, which is a most possible cause for schizophrenia (i.e., construct validity, similarities of the mechanism of onset); and (3) being capable of detecting an excellent drug efficacy of an atypical anti-psychotic agent rather than that of a typical anti-psychotic agent (predictive validity, predictability of clinical drug efficacy), is considered to be quite useful in the research and development of a therapeutic agent for cognitive dysfunction, a core symptom of schizophrenia, but such an animal model has not been known yet until now.

In animals, various tasks consisting of both of the training session, and the testing session being carried out after a prescribed period from the testing session, can be used in order to study a reference memory. In the training session, the animals are made to learn an avoidance response such as electroconvulsive shock (passive or active avoidance response), a task of reaching to a platform which is not visible below water (a water maze task), a task of fetching a food after getting through a maze task or a task of avoiding an electroconvulsive shock (radial maze task, Y or T maze task), a task of recognizing and searching a novel place or object, a task of pressing a lever for obtaining a food, etc., and further they are made to acquire the memory thereof. The animals are returned to exactly the same experimental environment after a prescribed period therefrom, and they are tested if they can retrieve the acquired memory. In the reference memory tasks, the animals can memorize all of the specific environment and stimulus which are given to them in a specific order in the training session. In order to correctly evaluate at the testing session the success and failure of the memory acquisition in the training session, it is necessary to carry out the training session and the learning session under exactly the same environment and stimulus. Especially, there is a report that animals show an abnormal memory retrieval when ethanol or an NMDA type receptor antagonist is administered only in the training session of the reference memory tasks, but not in the testing session (cf., Brain Res 706: 227-232 (1996), Pharmcol Biochem Behav 69: 585-593 (2001)). In such cases, the animals acquire a reference memory depending on the environment in the brain, which is induced by the administration of a drug, and in fact, it is proved that by administering a drug both in the training session and the testing session, the acquired memory can correctly be retrieved. Such a phenomenon is usually called state-dependency. In the evaluation of the reference memory functions, it is sometimes necessary to give sufficient consideration to the state-dependency in some cases, and it is necessary to avoid any artificial misjudgment on the evaluation of memory functions due to state-dependency. As mentioned above, in order to avoid any state-dependency effect by an agent for inducing memory/learning dysfunctions such as an NMDA type receptor antagonist, and to evaluate the reference memory/learning function, there is a method comprising administering an agent for inducing memory/learning dysfunctions in both of the training session and the testing session. Further, as an alternative method, it is easily speculated to utilize a method comprising chronically administering an agent for inducing memory/learning dysfunctions during the period including the training session and the testing session. In addition, instead of administering an agent for inducing memory/learning dysfunctions, it may be possible to utilize a method comprising expressing a chronic dysfunction during the period including the training session and the testing sessions of the reference memory tasks with the use of a gene engineering technique. For example, an NMDA type receptor subtype NR1 knockdown or NR2A subtype knockout animal are already produced as a concrete example for an animal model showing a chronic hypofunction of NMDA type receptor (cf., Cell 98: 427-436 (1999), J Neurosci 21: 750-757 (2001)).

DISCLOSURE OF INVENTION

The present invention provides a screening method of a therapeutic agent for memory/learning dysfunctions by schizophrenia. More particularly, the present invention provides an animal model for reference memory dysfunction caused by hypofunction of NMDA type receptor as a simple animal model for schizophrenia providing the predictability of the clinical drug efficacy of the existing therapeutic agents.

The present inventors have intensively studied in order to solve the above problems, and found that the reference memory dysfunction in the animals where NMDA type receptor hypofunction is induced both in the training session and the testing session is specifically improved by an atypical anti-psychotic agent but not by a typical anti-psychotic agent, and further they have confirmed that this evaluation system is a very simple and highly-reproducible evaluation system, and finally they have accomplished the present invention.

Namely, the present invention relates to the following features:

[1] An in vivo screening method for predicting whether or not a test compound is capable of improving the memory/learning dysfunctions by schizophrenia, wherein said method comprises a step of evaluating the memory/learning functions by employing a model showing glutamic acid N-methyl-D-aspartate (NMDA) type receptor hypofunction as an animal model for schizophrenia, and a reference memory task.

[2] The method according to the above [1], wherein the reference memory task is a passive avoidance task, an active avoidance task, a water maze task, a radial maze task, a T or Y maze task, a place recognition task, an object recognition task, an autoshaping learning task, or a lever-pressing task.

[3] The method according to the above [1], wherein the reference memory task is composed of two sessions of training and testing, and in the training session the animals are made to learn either of the tasks described in the above [2] and to acquire the memory of said task, and in the testing session being carried out after a prescribed period from the training session, the retention and retrieval ability of said memory of the animals are quantified.

[4] The method according to the above [1], wherein the model showing an NMDA type receptor hypofunction is produced by administering a compound having an NMDA type receptor antagonistic activity, e.g., MK-801, phencyclidine (PCP), ketamine, or a derivative thereof, to the animals in both of the training session and the testing session of the reference memory task, or by chronically administering said compound or a derivative thereof to the animals during the period including the training session and the testing session.

[5] The method according to the above [1], wherein the model showing an NMDA type receptor hypofunction is an animal model associated with an NMDA type receptor hypofunction due to variation, overexpression, or deficiency of gene of constitutive proteins or relevant proteins of an NMDA type receptor in both of the training session and the testing session of the reference memory task.

[6] A therapeutic agent for the memory/learning dysfunctions by schizophrenia, which comprises a substance selected by a screening method as set forth in any one of the above [1] to [5] as an active ingredient.

[7] A therapeutic agent for the memory/learning dysfunctions by schizophrenia, which comprises a serotonin 5-HT 1A antagonist selected by a screening method as set forth in any one of the above [1] to [5] as an active ingredient.

[8] A therapeutic agent for the memory/learning dysfunctions by schizophrenia, which comprises a choline acetylase inhibitor selected by a screening method as set forth in any one of the above [1] to [5] as an active ingredient.

[9] A therapeutic agent for the memory/learning dysfunctions by schizophrenia, which comprises aricept as an active ingredient.

[10] A therapeutic agent for the memory/learning dysfunctions by schizophrenia, which comprises quetiapine as an active ingredient.

[11] The therapeutic agent for the memory/learning dysfunctions by schizophrenia according to the above [10], which comprises as an active ingredient quetiapine in a daily dose of 5 to 270 mg.

[12] The therapeutic agent for the memory/learning dysfunctions by schizophrenia according to the above [10], which comprises as an active ingredient quetiapine in a daily dose of 15 to 90 mg.

[13] A therapeutic agent for the memory/learning dysfunctions by schizophrenia, which comprises clozapine as an active ingredient.

[14] The therapeutic agent for the memory/learning dysfunctions by schizophrenia according to the above [13], which comprises as an active ingredient clozapine in a daily dose of 0.2 to 34.5 mg.

[15] The therapeutic agent for the memory/learning dysfunctions by schizophrenia according to the above [13], which comprises as an active ingredient clozapine in a daily dose of 0.7 to 11.5 mg.

[16] A therapeutic agent for the memory/learning dysfunctions by schizophrenia, which comprises as an active ingredient an imide derivative of the formula [1]:

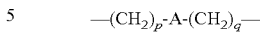

[1]

{wherein Z is a group of the formula:

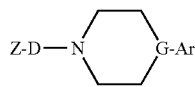

(in which B is a carbonyl or a sulfonyl; $R^1$ $R^2$, $R^3$ and $R^4$ are independently a hydrogen atom or a lower alkyl, provided that $R^1$ and $R^2$, or $R^1$ and $R^3$ may combine each other to form a hydrocarbon ring, or $R^1$ and $R^3$ may combine each other to form an aromatic hydrocarbon ring; said hydrocarbon ring may optionally be cross-linked with a lower alkylene or an oxygen atom; said lower alkylene and hydrocarbon ring may optionally be substituted by at least one alkyl; and n is 0 or 1), D is a group of the formula:

—(CH$_2$)$_p$-A-(CH$_2$)$_q$—

(in which A is a hydrocarbon ring optionally be cross-linked with a lower alkylene or an oxygen atom; said lower alkylene and said hydrocarbon ring may optionally be substituted by at least one alkyl; and p and q are independently 0, 1 or 2), G is N, CH or COH, and —Ar is an aromatic heterocyclic group, an aromatic hydrocarbon group, benzoyl, phenoxy, or phenylthio, or G is a carbon atom, and —Ar is a biphenylmethylidene, where said aromatic heterocyclic group, aromatic hydrocarbon group, benzoyl, phenoxy, phenylthio, and biphenylmethylidene may optionally be substituted by at least one group selected from a lower alkyl, a lower alkoxy and a halogen atom}, or an acid addition salt thereof.

[17] The therapeutic agent for the memory/learning dysfunctions by schizophrenia comprising as an active ingredient the imide derivative or an acid addition salt thereof according to the above [16], wherein Ar is an aromatic heterobicyclic group, naphthyl, benzoyl, phenoxy or phenylthio, and G is N, CH or COH, or —Ar is a biphenylmethylidene, and G is a carbon atom (said aromatic heterobicyclic group, naphthyl, benzoyl, phenoxy, phenylthio and biphenylmethylidene may optionally be substituted by at least one group selected from a lower alkyl, a lower alkoxy and a halogen atom).

[18] The therapeutic agent for the memory/learning dysfunctions by schizophrenia comprising as an active ingredient the imide derivative or an acid addition salt thereof according to the above [16], wherein Ar is an aromatic heterocyclic group condensed with a benzene ring, or naphthyl, benzoyl, phenoxy or phenylthio (said aromatic heterocyclic group condensed with a benzene ring, naphthyl, benzoyl, phenoxy, and phenylthio may optionally be substituted by at least one group selected from a lower alkyl, a lower alkoxy and a halogen atom), and G is N, CH or COH.

[19] The therapeutic agent for the memory/learning dysfunctions by schizophrenia comprising as an active ingredient the imide derivative or an acid addition salt thereof according to the above [16], wherein Z is a group of the formula:

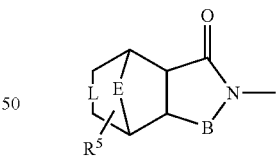

(in which -L- is a single bond or a double bond, E is a lower alkylene optionally substituted by a lower alkyl, or an oxygen atom, $R^5$ is a hydrogen atom or a lower alkyl, and B is the same as defined in the above [14]);

a group of the formula:

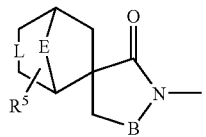

(in which -L-, E, $R^5$ and B are as defined above); a group of the formula:

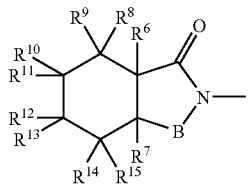

(in which $R^6$, $R^7$, $R^8$, $R^9$, $R^{10}$, $R^{11}$, $R^{12}$, $R^{13}$, $R^{14}$, $R^{15}$ are independently a hydrogen atom or a lower alkyl, or the adjacent two groups of $R^6$, $R^7$, $R^8$, $R^9$, $R^{10}$, $R^{11}$, $R^{12}$, $R^{13}$, $R^{14}$, $R^{15}$ may combine each other to form a double bond, and B is as defined above);
a group of the formula:

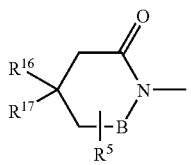

(in which $R^{16}$ and $R^{17}$ are independently a hydrogen atom or a lower alkyl, or $R^{16}$ and $R^{17}$ may combine each other to form a saturated hydrocarbon ring, and $R^5$ and B are as defined above); or
a group of the formula:

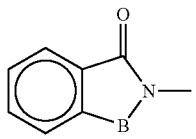

(in which B is as defined above).

[20] A therapeutic agent for the memory/learning dysfunctions by schizophrenia comprising as an active ingredient the imide derivative or an acid addition salt thereof, wherein the compound of the formula [1] is lurasidone:

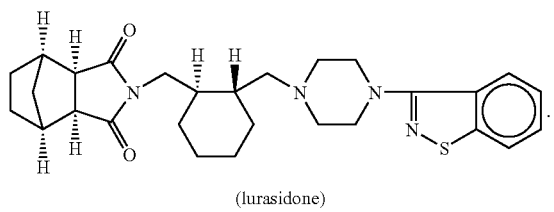

(lurasidone)

[21] A therapeutic agent for the memory/learning dysfunctions by schizophrenia, which comprises as an active ingredient a compound of the formula (2):

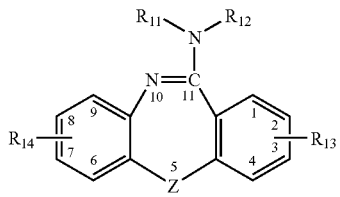

(2)

wherein Z is a divalent sulfur, imino, or lower alkylimino;
$R_{11}$ is a hydrogen atom or an alkyl having 1 to 5 carbon atoms;
$R_{12}$ is a hydrogen atom, an alkyl having 1 to 5 carbon atoms, a phenyl, an $R_{15}$-substituted phenyl, an aminoalkyl having 1 to 5 carbon atoms, a lower alkylaminoalkyl having 2 to 8 carbon atoms, a lower alkylamino, an amino, or a lower alkylamino; or $R_{11}$ and $R_{12}$ may combine each other together with N to form a 1-pyrrolidinyl, piperidino, morpholino, thiomorpholino, 1-piperazinyl, a 4-lower alkyl-1-piperazinyl, a 4-(hydroxy-lower alkyl)-1-piperazinyl or a 4-(lower alkoxy-lower alkyl)-1-piperazinyl; and
$R_{13}$, $R_{14}$, and $R_{15}$ are independently a hydrogen atom, a halogen atom, a hydroxy group, a trifluoromethyl, a lower alkyl, a lower alkoxy, or a lower alkylthio,
or an acid addition salt thereof.

The present invention provides a concrete method for evaluating a memory/learning improving activity being specific to certain atypical anti-psychotic agents but not to a typical anti-psychotic agent haloperidol. The results obtained by this method are in agreement with the clinical findings that haloperidol shows no improving activity of cognitive dysfunctions, and that atypical anti-psychotic agents exhibit an improving activity of cognitive dysfunctions. As a result, it becomes possible to provide a screening method of a therapeutic agent for cognitive dysfunctions by schizophrenia, and further provides a concrete therapeutic agent therefor. Actually, by the present method, the memory/learning improving efficacy is recognized with respect to lurasidone, which is under development as a candidate for a novel therapeutic agent for schizophrenia, noradrenaline α2 receptor antagonist 1-(2-pyrimidyl)piperazine dihydrochloride (hereinafter, referred to as 1-PP), and serotonin 5-HT 1A receptor antagonist in addition to risperidone, clozapine or quetiapine, by which a candidate for a novel agent for improving cognitive dysfunctions by schizophrenia can be provided. In addition, the memory/learning improving activity of clozapine and quetiapine is observed at a dose by 10 times or more lower than the dose at which they exhibit an anti-psychotic activity, and hence, a different action mechanism can be speculated. Further, since it is suggested that the retrieval of reference memory task being acquired with improvement by a drug is done with depending on the state of the NMDA type receptor hypofunction (state-dependent), as a novel and concrete method for evaluating the reference memory dysfunction improving activity of a drug, a method where the NMDA type receptor hypofunction is induced during the period including the training session and the testing session is effective.

BEST MODE FOR CARRYING OUT THE INVENTION

The present invention relates to an in vivo screening method for predicting whether or not a test compound is capable of improving the memory/learning dysfunctions by schizophrenia, wherein said method comprises a step of evaluating the memory/learning function by employing a model showing an NMDA type receptor hypofunction as an animal model for schizophrenia and a reference memory task.

The reference memory task includes, for example, a passive avoidance task, an active avoidance task, a water maze task, a radial maze task, a T or Y maze task, a place recognition task, an object recognition task, an autoshaping learning task, and a lever-pressing task.

The reference memory task is composed of two sessions such as training and testing. In the training session, an animal is made to learn a certain task and further made to acquire a memory thereof. After a prescribed period from the learning session, the testing session is carried out, and the retention and retrieval of the memory of task at the testing session is quantified.

A compound having an NMDA type receptor antagonistic activity, e.g., MK-801, PCP, ketamine, or a derivative thereof, is administered to animals during both in the training session and the testing session of the reference memory task, or chronically administered to animals during the period including the training session and the testing session, and these animals are used as an animal model showing an NMDA type receptor hypofunction.

Alternatively, an animal model associated with an NMDA type receptor hypofunction due to variation, overexpression or deficiency of gene of constitutive proteins or relevant proteins of NMDA type receptor in both of the training session and the testing session in the reference memory task can be used as a model showing an NMDA type receptor hypofunction.

Hereinafter, the present invention is illustrated in more detail by Examples, but the present invention should not be construed to be limited thereto.

Example 1

Method

Wistar male rats (7 weeks old) were used. Haloperidol (a typical anti-psychotic agent), clozapine, quetiapine, risperidon, olanzapine or aripiprazole (atypical anti-psychotic agent), or lurasidone being under development as a novel anti-psychotic agent was suspended in a 0.5% methyl cellulose (MC) and the resultant suspension was used as a test compound. Serotonin 5-HT 1A receptor antagonist WAY-100635 or noradrenaline a2 receptor antagonist 1-PP was dissolved in a physiological saline solution (Otsuka Pharmaceutical Co., Ltd.) and used as a test compound. As an NMDA type receptor antagonist, MK-801 hydrogen maleate (SIGMA-ALDRICH M-107) was dissolved in a physiological saline solution (Otsuka Pharmaceutical Co., Ltd.). A test compound (0.3 to 10 mg/kg) or a 0.5% MC or a physiological saline solution as a control was orally or interperitoneally administered to the animals one hour prior to the training session of the passive avoidance task, and MK-801 (0.05 mg/kg) or a physiological saline solution as a control was subcutaneously administered 30 minutes prior to both of the training session and the testing session. For the evaluation of state-dependency of MC-801, MK-801 was administered before the training session, and a physiological saline solution was administered before the testing session instead. The dosing value thereof was 5 ml/kg for each.

The step-through type passive avoidance response test was carried out in the following manners with the use of an apparatus consisting of a light-dark box, a slide door dividing the light-dark box and a shock generator (manufactured by O'hara & Co., Ltd., PA-2030A, PA-3001A) as an experimental apparatus. Namely, on Day 1 of the experiment, after a test compound and MK-801 were administered, the rats were put into the light box of the experimental apparatus where the back of each rat was directed to the dark box. Then, 10 seconds later, a slide door set at the border between the dark box and the light box was opened. Due to the habits of the rats, once the rats entered into the dark box, the slide door was quickly closed. At three seconds after entering into the dark box, an electroconvulsive shock (0.5 MA, for 3 seconds) was given to the rats. The period between the time just after the slide door was opened and the time at which the rats entered into the dark box was measured as a step-through latency. As to the animals which did not enter into the dark room even after 300 seconds, the training was terminated, and those animals were dropped in the following experiment for the reasons of training failure. On Day 2 of the experiment, the testing session was carried out about 24 hours after the training session. Thirty minutes prior to the testing session, MK-801 or a vehicle thereof, i.e., a physiological saline solution, was subcutaneously administered to the rats. The procedures of the testing session were carried out in the same manner to the training session except that no electroconvulsive shock was given. The step-through latency at the testing session was measured up to 300 seconds, and the step-through latency over 300 seconds was regarded as 300 seconds. The number of animals which showed 300 seconds at the testing session was counted, and the ratio thereof was calculated in percentages (as defined as a % of animals avoiding) in each group. The statistical analysis of the % of animals avoiding was done by $x^2$ test with Bonferroni's correction. The animals were used in a group of 10 to 25 animals per group, and the data was expressed by percentage.

(Results)

First, a drug was administered alone without MK-801, and a dose of the drug to induce the memory/learning dysfunctions in the passive avoidance response was determined. Further a dose less than that dose and to induce no memory/learning dysfunctions was used as an administration dose in the MK/801 models (Table 1).

The animals to which MK-801 was administered before the training session, and a physiological saline solution was administered before the testing session showed the nearly equal decrease in the step-through latency to that of the animals to which MK-801 was administered both in the training session and the learning session. That is, it was found that the memory dysfunction observed in the cases where MK-801 was administered only before the training session, or before both of the training session and the testing sessions, is not a memory retrieval dysfunction but memory acquisition dysfunction.

Next, the effects of drugs on the memory dysfunction observed in the cases where MK-801 was administered in both of the training session and the testing session were studied. In the group to which MK-801 was not administered, the animals showing 300 seconds of step-through latency (% of animals avoiding) was 75 to 80% in all of the experiments. On the contrary, the % of animals avoiding became 0 to 5% in all of the experiments by the administration of MK-801. The effects of the test compounds on the % of animals avoiding were shown in Table 1. As is shown in Table 1, there were differences of the drug efficacy strength among individual drugs. That is, while no drug efficacy was observed with respect to either a typical anti-psychotic agent haloperidol, or atypical anti-psychotic agents olanzapine, aripiprazole, but a significant improving activity was observed with respect to atypical anti-psychotic agents clozapine, quetiapine, lurasidone, and serotonin 5-HT 1A receptor antagonist WAY-100635, noradrenalin α2 receptor antagonist 1-PP.

Interestingly, it is known that a dose to inhibit 50% of methamphetamine-induced hyperponesis in rats (ED50, mg/kg, p.o.), which reflects anti-psychotic activity, is 65 and about 100 with respect to clozapine and quetiapine, respectively. That is, it is suggested that clozapine and quietiapine show a memory/learning dysfunction improving activity at a dose 65-272 times or 10 times lower than the dose thereof showing anti-psychotic activity, ED50, respectively. Thus, it became apparent that these drugs show its memory/learning dysfunction improving activity in a different action mechanism from that of the anti-psychotic activity thereof. Since the clinical daily dose of clozapine as an anti-psychotic agent is 150-750 mg, then a dose thereof for improving memory/learning dysfunctions by schizophrenia should be 0.2-34.5 mg, preferably 0.7-11.5 mg, which are obtained by calculating 150/217-750/65 (i.e., 0.7-11.5 mg) and broadening the obtained range into either direction by about 3 times. On the other hand, since the clinical daily dose of quetiapine as an anti-psychotic agent is 150-900 mg, then a dose thereof for improving memory/learning dysfunctions by schizophrenia should be 5-270 mg, preferably 15-90 mg, which is obtained by calculating 150/10-900/10 (i.e., 15-90 mg) and broadening the obtained range into either direction by about 3 times.

Finally, with respect to lurasidone and 1-PP, which showed the most remarkable memory/learning dysfunction improving activity, when the effects thereof on the memory dysfunction in cases where MK-801 was administered only in the training session were studied, either of these drugs showed no drug efficacy. From these results, it was proved that the memory of passive avoidance response being acquired with improvement by lurasidone and 1-PP depends on the state of MK-801 administration, i.e., state-dependent.

Example 2

In the procedures of Example 1, PCP HCl (0.75 mg/kg) was subcutaneously administered instead of MK-801 (0.05 mg/kg) to animals prior to both of the training session and the testing session of the memory/learning task to induce memory/learning dysfunctions, and the memory/learning dysfunction improving activity of a test compound can be evaluated.

Example 3

The memory/learning dysfunction improving activity of a test compound can be evaluated under the exactly same conditions as those in Examples 1 and 2, except that ketamine is used instead of MK-801 or PCP HCl.

Example 4

In the procedures of Examples 1 to 3, instead of subcutaneous administration of an NMDA type receptor antagonist such as MK-801, PCP HCl or ketamine prior to both of the training session and the testing session, these drugs are injected to an ALZET osmotic pump and implanted under the skin of the back side of the animals so that these drugs are chronically administered under the skin during the period including the training session and the testing session, and a memory/learning dysfunctions can be induced thereby, and then the memory/learning dysfunction improving activity of a test compound thereon can be evaluated.

Example 5

Instead of the method of using an NMDA type receptor antagonist as shown in the above Examples, an animal showing a variation, overexpression or deficiency of gene of constitutive proteins or relevant proteins of the NMDA type receptor can be utilized.

Example 6

In the procedures of Examples 1 to 5, either one of an active avoidance task, a water maze task, a radial maze task, a T or Y maze task, a place recognition task, an object recognition task, an autoshaping learning task, and a lever-pressing task can be employed instead of a passive avoidance task, and the exactly same experiment as Example 1 can be carried out.

Table 1 shows the effects of the drugs on MK-801-induced memory/learning dysfunctions in the passive avoidance task in rats.

To be more precise, Table 1 shows the effects of the drugs in terms of the percentage of the animals acquiring passive avoidance response (i.e., the percentage of the animals showing a step-through latency of 300 seconds or more in the testing session, that is, the percentage of the animals showing a remarkable memory retention, a % of animals avoiding) in the passive avoidance response test in the rats to which MK-801, an NMDA type receptor antagonist, was administered prior to both of the training session and the testing session.

In a similar passive avoidance response test, a minimum dose of a drug to induce memory/learning dysfunctions by a single application thereof is shown in the right edge column of Table.

The figures in Table mean a % of animals avoiding. In a similar passive avoidance response test, a minimum dose of a drug to induce memory/learning dysfunctions by a single application thereof is shown in the right edge column of Table.

TABLE 1

| Drug | Vehicle group | Group treated with MK-801 (0.05 mg/kg, s.c.) | Groups treated with MK-801 + Drug (mg/kg, p.o.) | | | | | Minimum dose to induce memory dysfunction by single application, mg/kg, p.o |
|---|---|---|---|---|---|---|---|---|
| | | | 0.1 | 0.3 | 1 | 3 | 10 | |
| (MK-801 administered prior to training session) | | | | | | | | |
| Lurasidone | 80 | 0 | — | 20 | 20 | 30 | 20 | >30 |
| 1-PP | 92 | 0 | — | — | — | 8 | — | — |
| (MK-801 administered prior to both of training and testing sessions) | | | | | | | | |
| Haloperidol | 80 | 0 | 0 | 5 | 15 | 10 | — | 10 |
| Olanzapine | 80 | 0 | — | 15 | 20 | 20 | 10 | 3 |
| Risperidone | 76 | 4 | 20 | 20 | 28 | 10 | — | 3 |
| Clozapine | 80 | 4 | — | 44* | 36* | 20 | 10 | 10 |
| Quetiapine | 75 | 5 | — | 10 | 20 | 30 | 50* | 30 |
| Aripiprazole | 80 | 4 | — | — | 16 | 16 | — | 10 |
| Lurasidone | 80 | 0 | — | 40* | 35* | 75* | 70* | >30 |
| 1-PP | 80 | 13 | — | — | 47* | 67* | — | — |
| WAY-1000635 | 75 | 5 | — | 30 | 40* | 30 | — | — | n = 10-25
*P < 0.05 vs Group treated with MK-801 (0.05 mg/kg s.c.)

INDUSTRIAL APPLICABILITY

The present invention provides an in vivo screening method of a therapeutic agent for improving memory/learning dysfunctions by schizophrenia.

What is claimed is:

1. A method for improving memory or learning dysfunctions caused by schizophrenia, comprising administering lurasidone, or an acid addition salt thereof, to a patient suffering from memory or learning dysfunctions caused by schizophrenia.

2. The method of claim 1, in which the patient is administered a dose of from 0.3 to 10 mg/kg per os.

3. A method for improving memory or learning dysfunctions caused by schizophrenia, comprising administering lurasidone, or an acid addition salt thereof, to a patient suffering from memory or learning dysfunctions caused by schizophrenia, in which administering lurasidone induces neither memory dysfunction nor learning dysfunction.

* * * * *